United States Patent
Caratsch et al.

(12) 
(10) Patent No.: US 6,403,035 B1
(45) Date of Patent: Jun. 11, 2002

(54) APPARATUS FOR TRANSPORTING COMPONENTS WITHIN AN AUTOMATIC ANALYZER SYSTEM

(75) Inventors: Thomas Caratsch, Mettmenstetten; Peter Vischer, Küssnacht am Rigi, both of (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/396,157

(22) Filed: Sep. 14, 1999

(30) Foreign Application Priority Data

Sep. 28, 1998 (EP) .............................. 98810974

(51) Int. Cl.⁷ .............................................. G01N 35/00
(52) U.S. Cl. ............................ 422/65; 436/43; 436/47
(58) Field of Search .......................... 422/65; 436/43, 436/47; 198/690.1, 465.2

(56) References Cited

U.S. PATENT DOCUMENTS

| | | | |
|---|---|---|---|
| 5,207,986 A | 5/1993 | Kadota et al. ............... 422/65 |
| 5,429,010 A | 7/1995 | Löhndorf et al. .......... 73/866.5 |
| 5,735,387 A | * 4/1998 | Polaniec et al. ......... 198/690.1 |
| 6,117,683 A | * 9/2000 | Kodama et al. .............. 436/47 |
| 6,220,451 B1 | * 4/2001 | Hoffmann ................... 209/522 |
| 6,267,927 B1 | * 7/2001 | Longedo et al. .............. 422/65 |

FOREIGN PATENT DOCUMENTS

| | | |
|---|---|---|
| DE | 3841961 A 1 | 6/1990 |
| DE | 19742160 A 1 | 4/1998 |
| EP | 0 856 736 A | 8/1998 |
| WO | WO 93 15407 | 8/1993 |
| WO | WO 98 01760 | 1/1998 |

OTHER PUBLICATIONS

Copy of 2 Slides Shown at PCR Symposium in Basle, Switzerland on Nov. 26, 1998.

* cited by examiner

Primary Examiner—Nina Bhat
(74) Attorney, Agent, or Firm—Gibbons, Del Deo, Dolan, Griffinger & Vecchione (57) ABSTRACT

The present invention refers to an apparatus for transporting components within an automatic analyzer system. In order to provide a simple and low cost apparatus for transporting components within an automatic analyzer system, the apparatus comprises a component carrier suitable for holding a plurality of components; transport means for transporting the component carrier from a first position in a first apparatus which has a first housing and forms part of the analyzer system to at least a second position in a second apparatus which has a second housing and also forms part of the analyzer system; and a third housing containing the transport means and connected with the first housing of the first apparatus and aligned with the second housing of the second apparatus.

26 Claims, 12 Drawing Sheets

APPARATUS FOR TRANSPORTING COMPONENTS WITHIN AN AUTOMATIC ANALYZER SYSTEM

FIELD OF THE INVENTION

The present invention relates to an apparatus for transporting components within an automatic analyzer system for analyzing biological samples. The system comprises at least two apparatuses which form part of that system, wherein at least one of the apparatuses includes means for automatically analyzing the biological samples.

BACKGROUND OF THE INVENTION

Since not all possible analyses can be performed with a single analyzer, the equipment used by laboratories often comprises a plurality of specialized analyzers of various types and additional equipment for performing preliminary operations such as preparation of biological samples before they are introduced into specialized analyzers. In order to satisfy the equipment needs of laboratories, such equipment has to be available in a great diversity of configurations. Also, it should be possible to modify an initial configuration and to supplement it with additional equipment if and when necessary.

Moreover, various system components such as sample tubes, reagent containers, and accessories like disposable pipetting tips often have to be transferred from one apparatus forming part of the analyzer system to another.

Since a high degree of automation is desirable in laboratories where clinical chemistry analyses are performed on large numbers of patient samples, the situation described above gives rise to the need for means for transporting system components, e.g. sample tubes, reagent containers, disposable pipetting tips, etc., from one of the apparatuses forming part of the analyzer system to at least another one of the apparatuses forming part of the analyzer system.

Transport means like robot arms and grippers known in the prior art for transporting components in analyzer systems have two major disadvantages. On the one hand, they are relatively expensive because they require high cost components like sensors and complex control means. On the other hand, known transport systems require very accurate mechanical adjustments and installation work in order to operate successfully.

SUMMARY OF THE INVENTION

The aim of the present invention is to provide a simple and low cost apparatus for transporting components within an automatic analyzer system.

According to the invention, this aim is achieved with an apparatus which comprises:

(a) a component carrier for holding the components,
(b) transport means for transporting the component carrier from a first position in a first apparatus which has a first housing and forms part of the analyzer system to at least a second position in a second apparatus which has a second housing and which forms part of the analyzer system, and
(c) a third housing containing the transport means, the third housing being connected with the first housing of the first apparatus and being aligned with the second housing of the second apparatus.

A main advantage of the apparatus according to the present invention is that it provides very effective transport means at a relatively low cost because the invention does not require expensive sensor components or accurate mechanical adjustments and installation work in order to operate successfully.

DETAILED DESCRIPTION OF THE INVENTION

Figure 1:
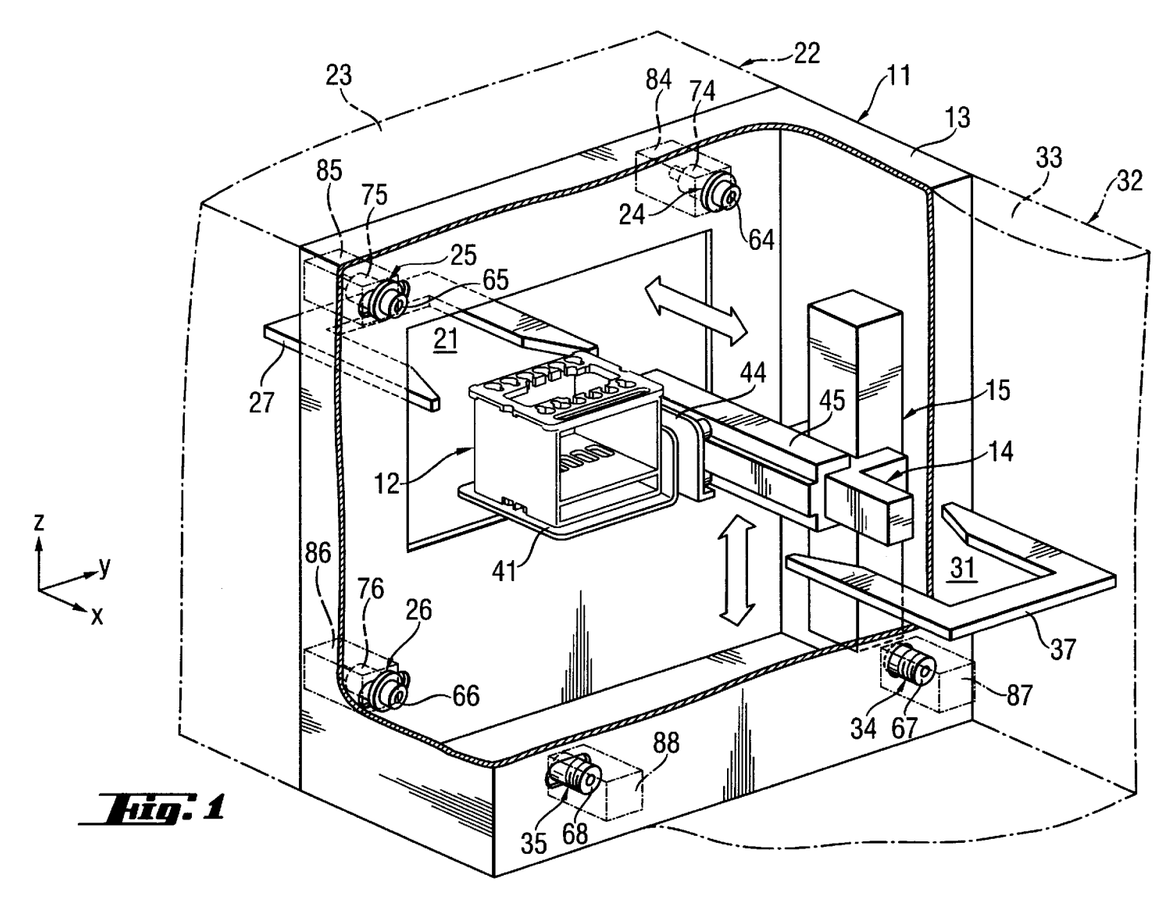
FIG. 1 is a schematic view of an embodiment of an apparatus according to the invention arranged between a first apparatus and a second apparatus which form part of an analyzer system.

FIG. 1 schematically represents an apparatus 11 according to the present invention for transporting components within an automatic analyzer system. Apparatus 11 is arranged between a first apparatus 22 and a second apparatus 32 which both form part of an analyzer system. Apparatus 11 comprises a component carrier 12 suitable for holding a plurality of components, and transport means 41, 14, and 15 for transporting component carrier 12 from a first position 21 in apparatus 22 to at least a second position 31 in apparatus 32.

The first position 21 is preferably at a predetermined position in a loading bay 27 mounted on apparatus 22. Loading bay 27 serves for receiving component carrier 12 when it is brought to it by transport means 41, 14, and 15.

The second position 31 is preferably at a predetermined position in a loading bay 37 mounted on apparatus 32. Loading bay 37 serves for receiving component carrier 12 when it is brought to it by transport means 41, 14, and 15.

Apparatus 22 has a housing 23. Apparatus 32 has a housing 33. Apparatus 11 has a housing 13 which contains transport means 41, 14, and 15. Housing 13 is connected with housing 23 of apparatus 22 and aligned with housing 33 of apparatus 32. As described hereinafter, an apparatus according to the invention can be connected to more than 2 apparatuses which form part of the analyzer system.

Figure 2:
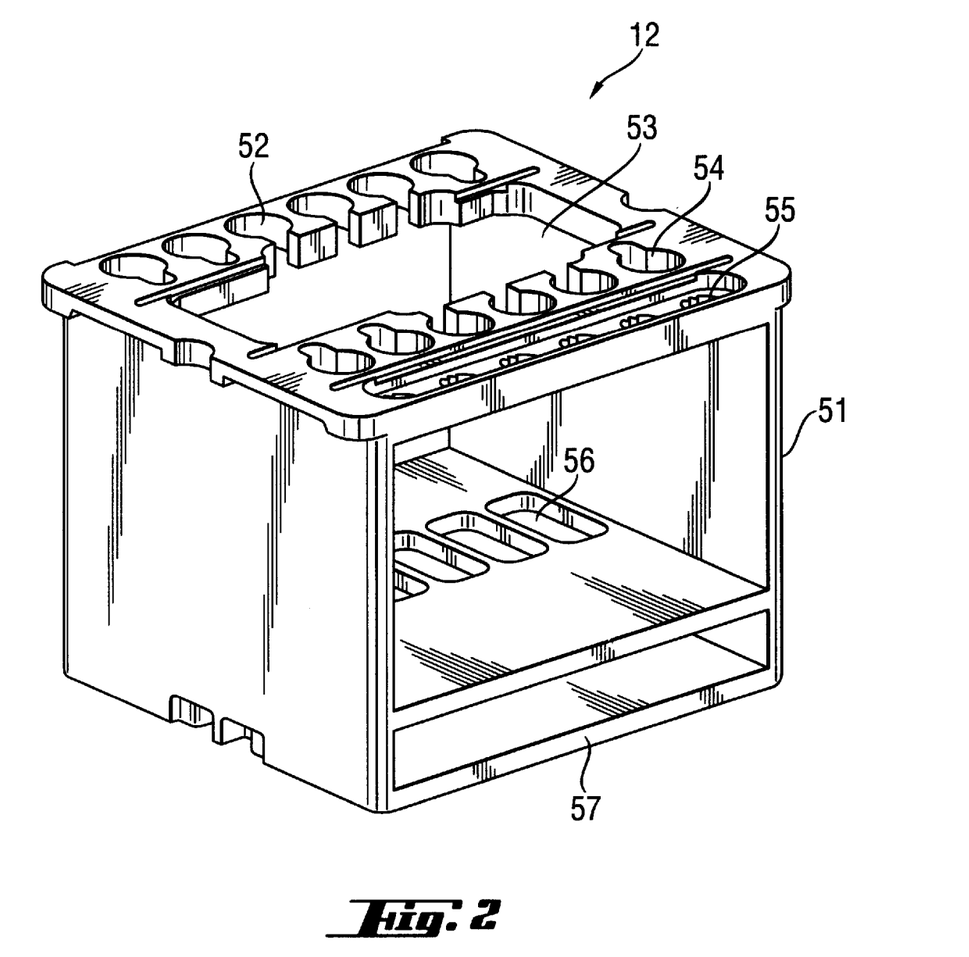
FIG. 2 is a schematic view of a component carrier which forms part of an apparatus in FIG. 1.

As shown in FIG. 2, a preferred embodiment of component carrier 12 has the general shape of a hollow box 51 with various openings 52–55 and chambers 56 suitable for holding a plurality of components of different shapes and sizes. Box 51 has a bottom wall 57. The outer surface of bottom wall 57 comprises at least one metallic part (not shown in the drawings) which is apt to be attracted and held by a magnetic force.

Figure 3:
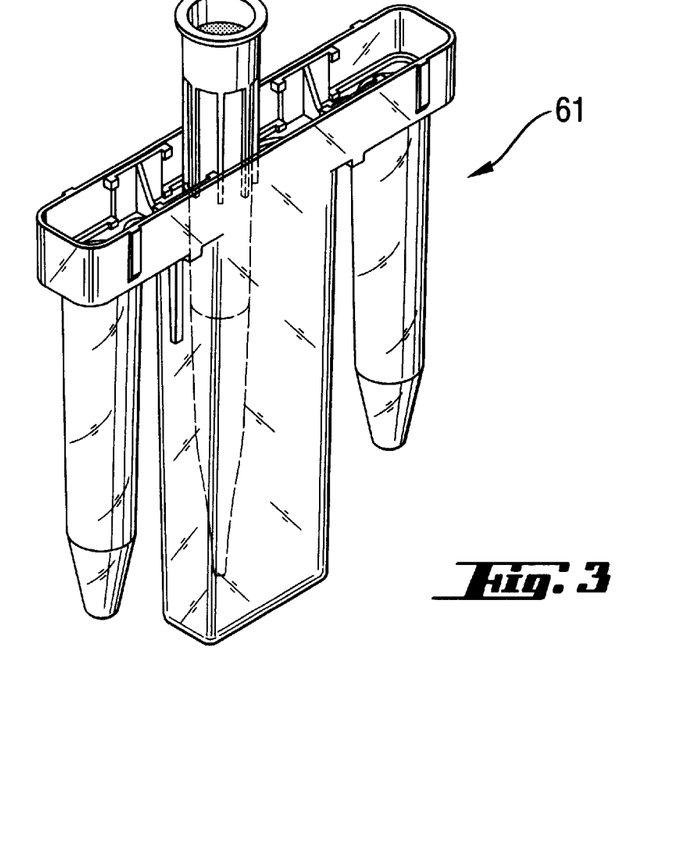
FIG. 3 is a schematic view of a first component which is apt to be carried by a component carrier shown in FIGS. 1 and 2.

FIG. 3 shows a first example of a component which can be inserted in and transported by component carrier 12. The component 61 shown in FIG. 3 is a specimen processing unit of the type used in an apparatus for separating nucleic acid from a sample cell material.

Figure 4:
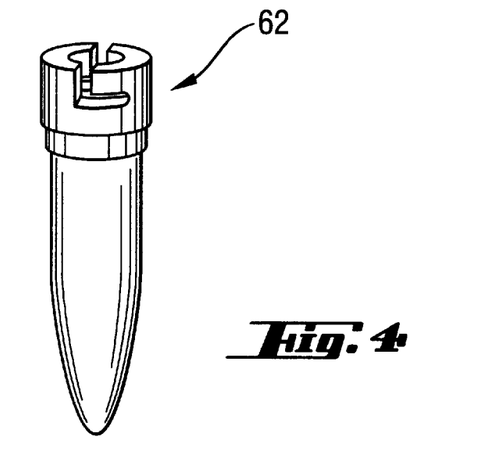
FIG. 4 is a schematic view of a second component which is apt to be carried by a component carrier shown in FIGS. 1 and 2.

FIG. 4 shows a second example of a component which can be inserted in and transported by component carrier 12. The component 62 shown in FIG. 3 is a sample tube of the type used in an apparatus for separating nucleic acid from a sample cell material.

Figure 5:
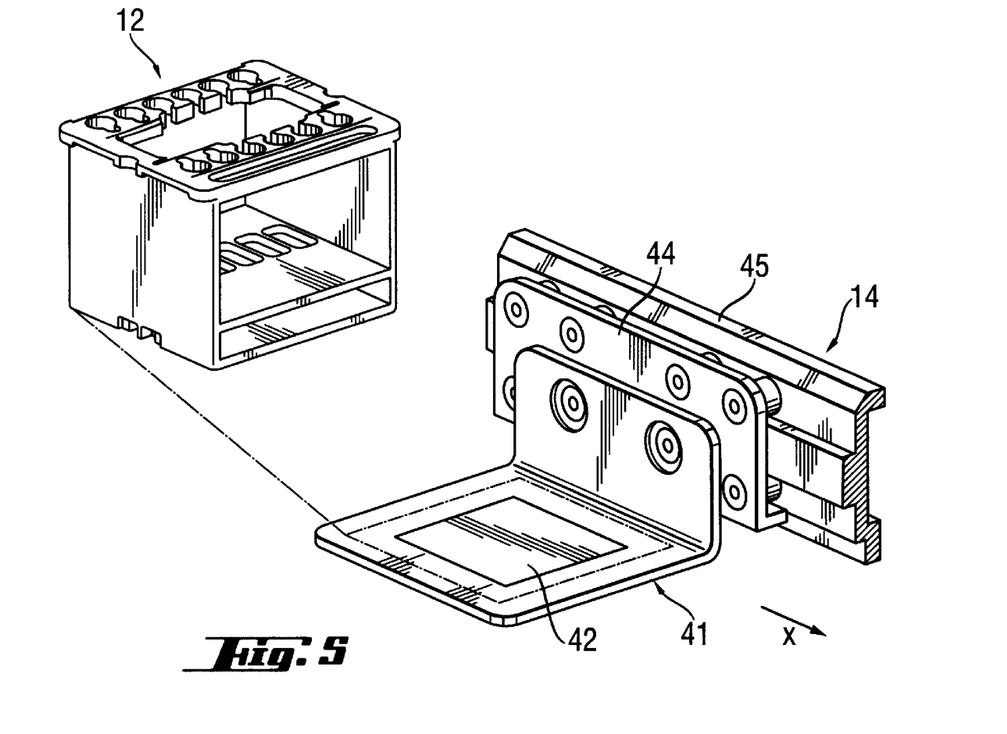
FIG. 5 is a schematic view of a tray and component carrier shown in FIG. 1

As shown in FIG. 1, the above-mentioned transport means for transporting component carrier 12 comprise a movable tray 41 for holding component carrier 12 and for moving it from position 21 to position 31. To achieve this, tray 41 has an upper surface which is at least partially covered by a magnetic foil 42 as shown by FIG. 5. During transport of component carrier 12 on tray 41, the magnetic force exerted by magnetic foil 42 on at least one metallic part on the outer surface of the bottom wall of component carrier 12 holds the carrier on tray 41 until it is properly positioned in one of the loading bays 27 or 37. The magnetic force exerted by foil 42 is strong enough to ensure that component carrier 12 is kept on tray 41 during its transport. Component carrier 12 is, however, revolvable about the Z-axis and is free to be moved along the X and Y axes, respectively.

Figure 6:
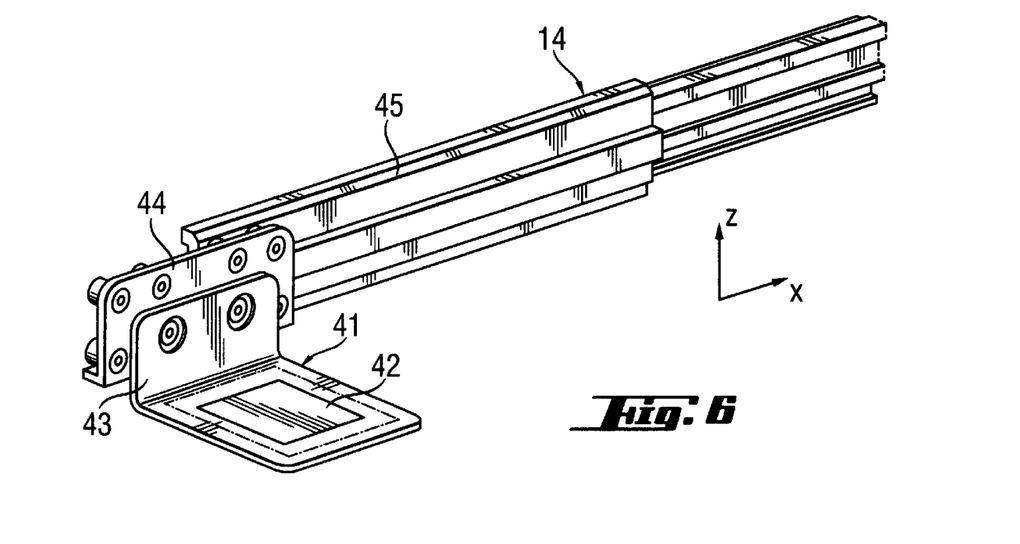
FIG. 6 is a schematic view of a telescopic arm which is an embodiment of the horizontal drive means shown in FIG. 1.

As can be further appreciated from FIG. 1, the above-mentioned transport means for transporting component carrier 12 further comprise a transport device 14 for moving said tray 41 back and forth in a horizontal direction along the X-axis towards and away from each of loading bays 27 and 37, respectively. A preferred embodiment of transport device 14 is a telescopic arm 45 which has a movable part 44 and which is shown in FIG. 6. Tray 41 with its plate 43 is attached to movable part 44 of telescopic arm 45. Telescopic arm 45 moves part 44 horizontally in an X-direction as shown in FIG. 6. In order to bring a component carrier 12 from loading bay 27 on one side of apparatus 11 to a loading bay 37 on the opposite side of apparatus 11, telescopic arm 45 is adapted to extend its outer end to both sides of apparatus 11. On its way from one loading bay to the other, movable part 44 of telescopic arm 45 passes through the middle of apparatus 11.

Figure 7:
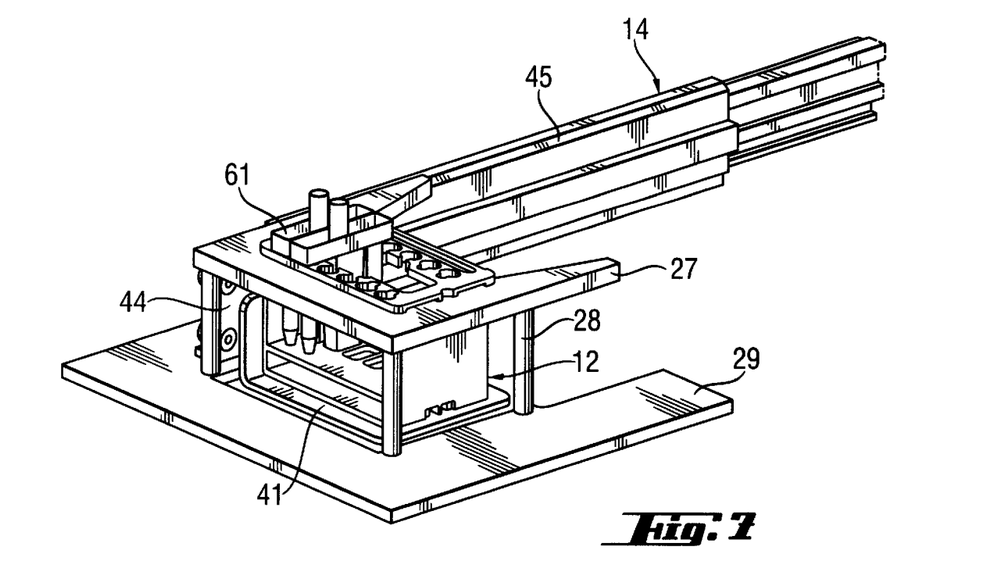
FIG. 7 is a schematic view showing use of a telescopic arm shown in FIG. 6 for positioning a component carrier in a loading bay shown in FIG. 1.

FIG. 7 illustrates a positioning of component carrier 12 in loading bay 27 by means of tray 41 moved by means of telescopic arm 45. As depicted in FIG. 7, loading bay 27 is mounted by supports 28 on a plate 29. Plate 29 is mounted on apparatus 22.

Figure 8:
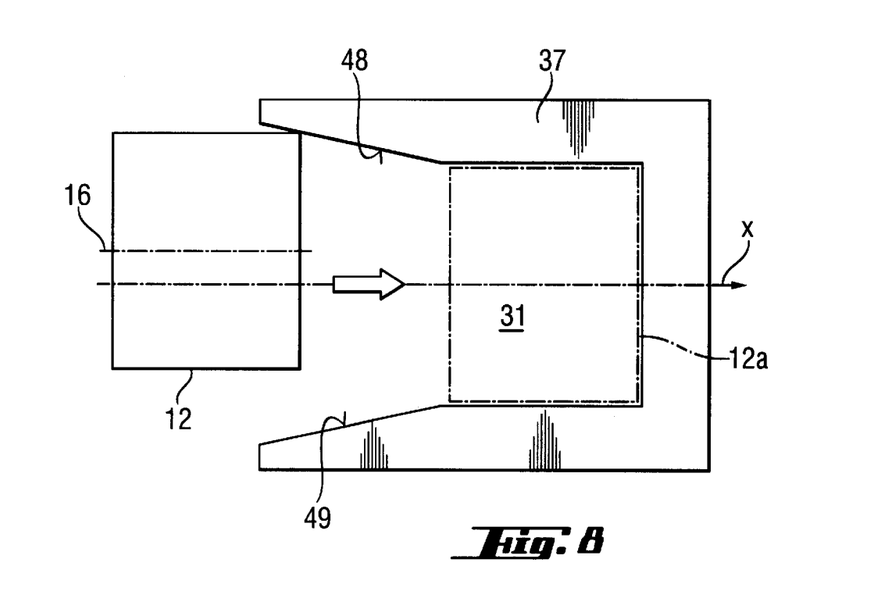
FIG. 8 is a schematic top view showing introduction of a component carrier in a loading bay shown in FIG. 1.

FIG. 8 illustrates a positioning of component carrier 12 in loading bay 37. According to the invention, the transport means do not require that component carrier 12 be perfectly aligned with the position it has to eventually occupy in loading bay 37. In a preferred embodiment, each of the loading bays 27 and 37 has guide surfaces which bring component carrier 12 into alignment with that position as component carrier 12 is moved by tray 41 and telescopic arm 45 into position 31 in loading bay 37. Broken line rectangle 12a illustrates the position taken by carrier 12 when it reaches position 31.

Figure 8A:
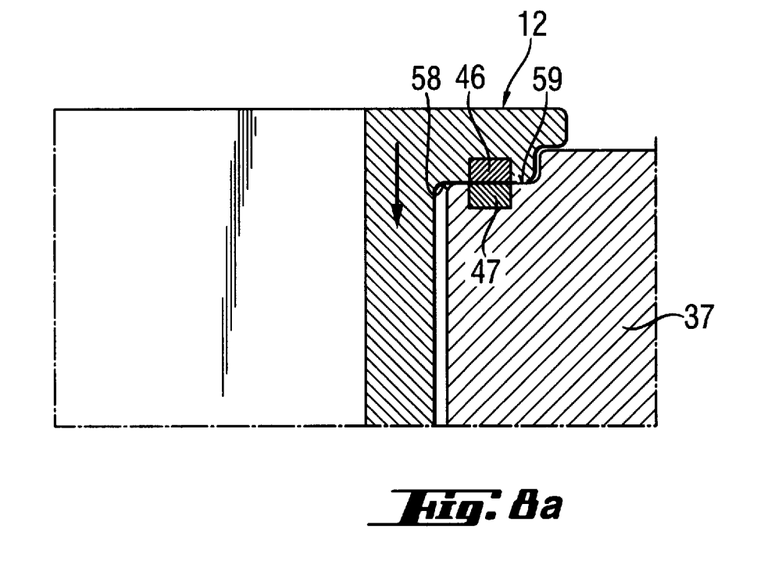
FIG. 8a is a partial cross-sectional view showing the shape of the parts of a component carrier and a loading bay which cooperate with each other when a carrier is positioned in a loading bay.

FIG. 8a shows a partial cross-sectional view of component carrier 12 and loading bay 37 in a plane normal to the X-axis in FIG. 8 when carrier 12 reaches position 12a in FIG. 8.

As shown in FIG. 8a, component carrier 12 has side walls each of which has at its upper end a shoulder 58 which rests on a top surface 59 of loading bay 37. A ferromagnetic metal piece 46 is lodged in at least one recess of shoulder 58. When carrier 12 reaches its predetermined position in an X-direction with respect to the loading bay 37, a metal piece 46 lies in front of a permanent magnet 47 which is lodged in at least one recess of top surface 59 of loading bay 37.

As shown in FIG. 8a, top surface 59 of the loading bay is shaped so that it matches the shape of shoulder 58.

Positioning of component carrier 12 at position 31 in loading bay 37 by means of the above-mentioned transport means is performed in two steps. In a first step, carrier 12 is moved in an X-direction towards loading bay 37 as represented in FIG. 8. During this step, carrier 12 is maintained at a constant height (in the Z-direction) at which shoulder 58 lies at a predetermined distance from and above top surface 59. Guide surfaces 48 and 49 guide carrier 12 so that when it reaches position 31 in loading bay 37 the symmetry axis 16 of carrier 12 substantially coincides with the central axis of loading bay 37 which coincides with the X-axis represented in FIG. 8. In a second step, carrier 12 is slowly lowered. During this step, top surface 59 of loading bay 37 guides shoulder 58 of carrier 12 and at a given point metal piece 46 of carrier 12 is attracted and held by magnet 47 of loading bay 37. In this way, carrier 12 eventually reaches its final position 31 in loading bay 37 in all three directions (X-, Y- and Z-direction).

Figure 9:
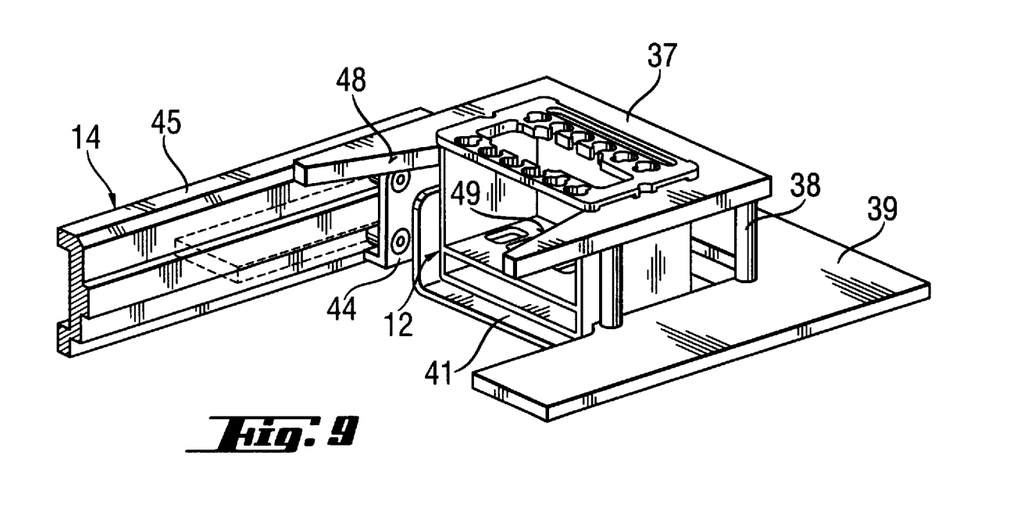
FIG. 9 is a schematic view showing a component carrier positioned in a loading bay shown in FIG. 1.

FIG. 9 shows component carrier 12 duly positioned in loading bay 37. As shown, loading bay 37 is mounted by supports 38 on a plate 39. Plate 39 is mounted on apparatus 32.

As illustrated in FIG. 1, the above-mentioned transport means for transporting component carrier 12 further comprise a transport device 15 for moving the tray 41 upwards and downwards in a vertical direction along the Z-axis.

Figure 10:
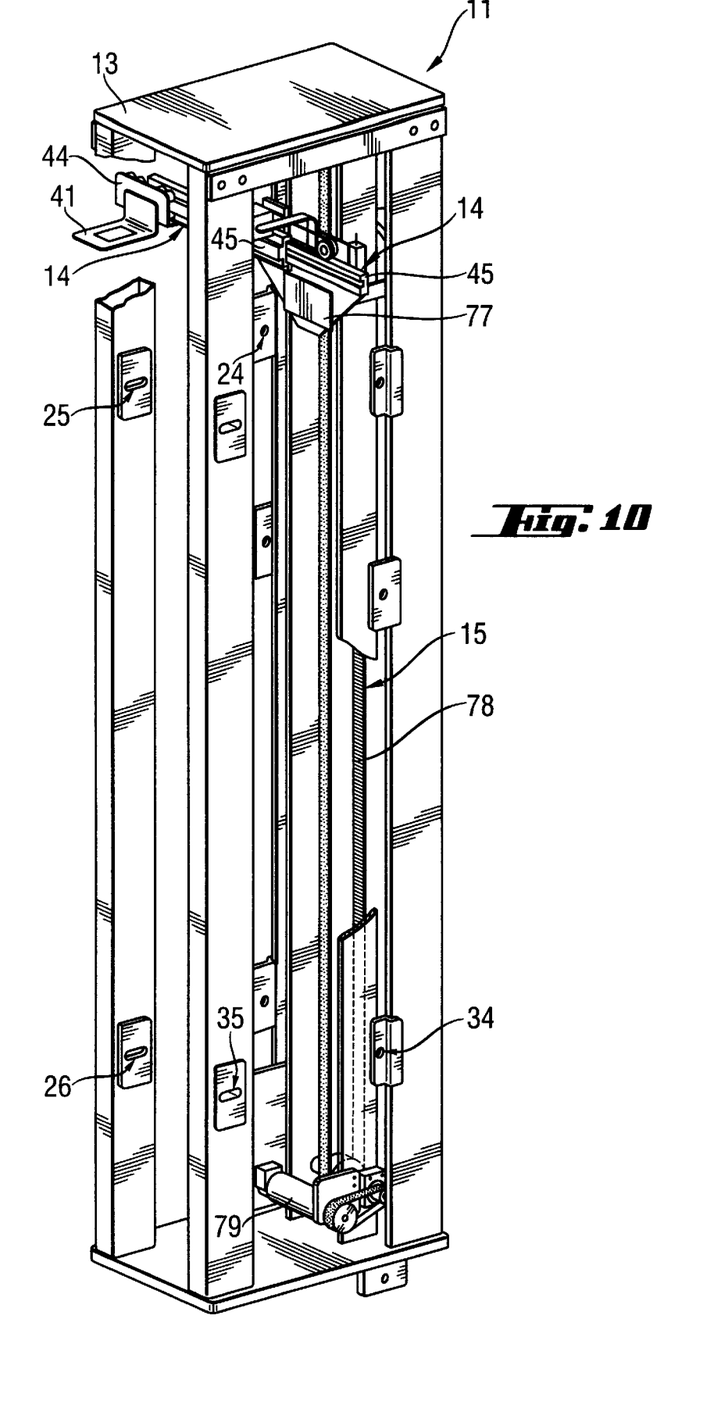
FIG. 10 is a schematic view of an embodiment of an apparatus according to the invention.

FIG. 10 shows a preferred embodiment of an apparatus 11 according to the invention. FIG. 10 shows more detail of the above-mentioned transport means 14 and 15.

Transport device 15 comprises a carriage 77 which is moved upwards and downwards in the vertical direction along the Z-axis by means of a toothed belt 78 driven by a gearmotor 79.

Figure 11:
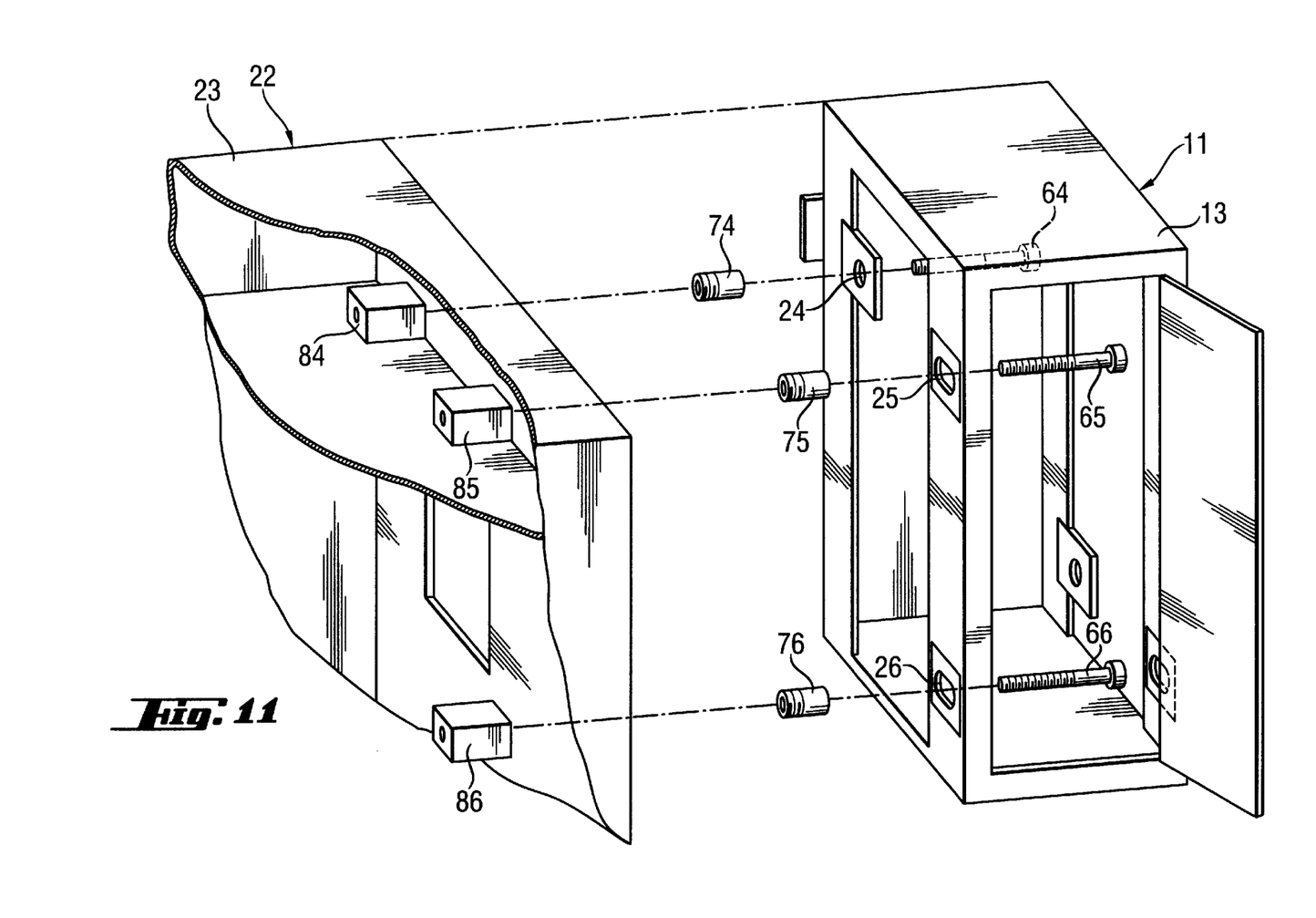
FIG. 11 is a schematic view illustrating the connection of an apparatus according to the invention to a first apparatus which forms part of an analyzer system.

As shown in FIG. 1, housing 13 of apparatus 11 in FIG. 1 is connected to housing 23 of apparatus 22 by means of screw connections 24, 25, and 26. These connections are represented in more detail in FIG. 11, which shows screws 64, 65, and 66; bolts 74, 75, and 76; and bolt holders 84, 85, and 86 used to build screw connections 24, 25, and 26.

Figure 12:
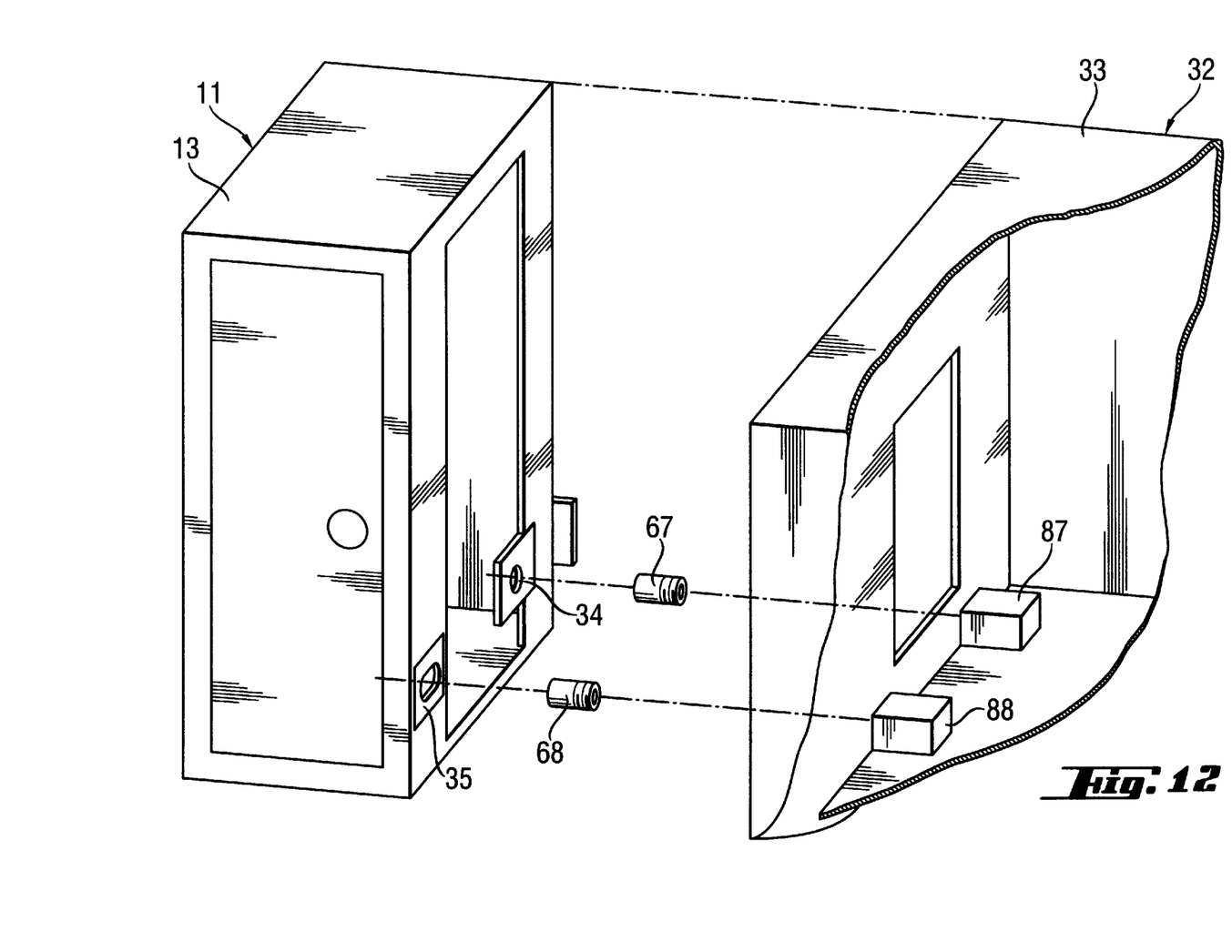
FIG. 12 is a schematic view illustrating the connection of an apparatus according to the invention to a second apparatus which forms part of an analyzer system.

As shown in FIG. 1, housing 13 of apparatus 11 in FIG. 1 is aligned to housing 33 of apparatus 32 by means of bolts 34 and 35. This alignment is represented in more detail in FIG. 12 which shows bolts 67 and 68 and bolt holders 87 and 88 used to build contacts 34 and 35.

The advantage of the above-mentioned screw and bolt connections is that they permit alignment of apparatuses 22 and 32, each of which have considerable weight, with apparatus 11. According to the invention, the alignment is achieved with the necessary accuracy, without special alignment equipment, and so that even when the apparatuses are connected and properly aligned with respect to each other, each of the apparatuses stands on its own individual base. The above-mentioned screw and bolt connections prevent the apparatus walls, which are in contact with each other, from having to bear unnecessary and unpredictable contact forces to achieve alignment. Preventing such forces from arising is advantageous because it eliminates the need for reinforcement of the frame structures of the apparatuses, which would otherwise be necessary.

An apparatus according to the invention can be used in various configurations with at least two apparatuses which form part of an analyzer system.

Figure 13:
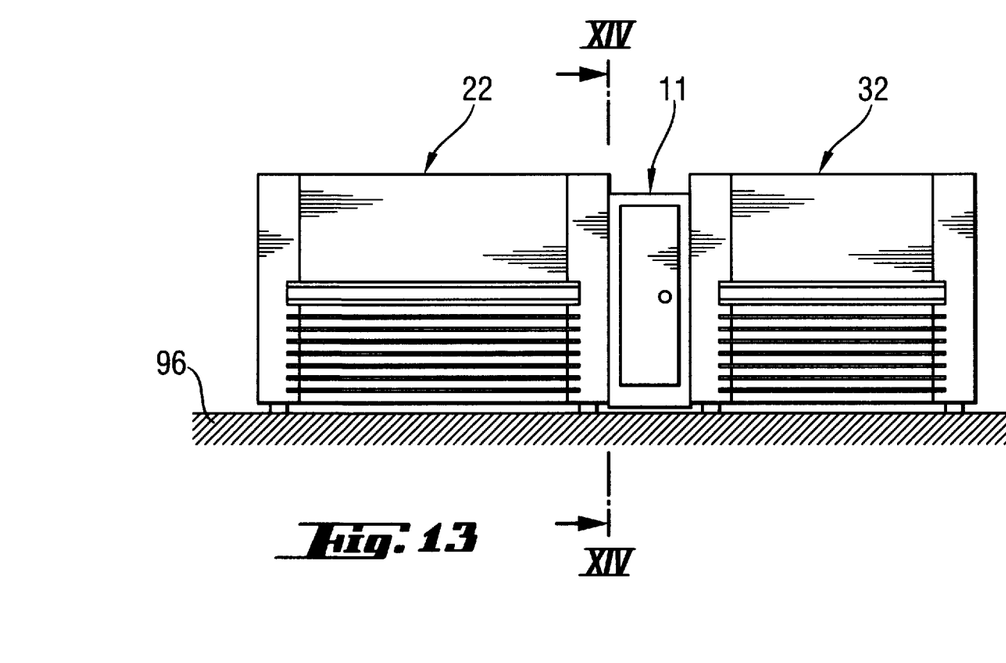
FIG. 13 is a schematic front view showing an embodiment of an apparatus according to the invention arranged between a first apparatus and a second apparatus which form part of an analyzer system.
Figure 14:
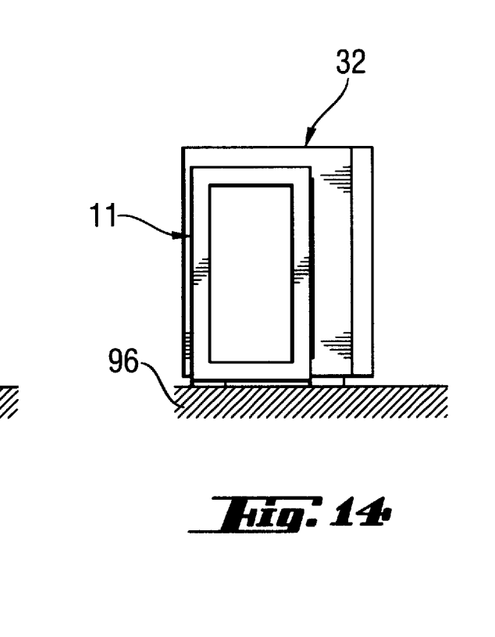
FIG. 14 is a schematic cross-sectional view in plane XIV—XIV of apparatuses shown in FIG. 13.

FIG. 13 shows a first configuration wherein a first embodiment of an apparatus 11 according to the invention is arranged between an apparatus 22 and an apparatus 32 which form part of an analyzer system. All three apparatuses are positioned on a table 96. Apparatus 11 provides the means for transporting a component carrier of the type described above between apparatuses 22 and 32. FIG. 14 shows a side view of apparatuses 11 and 32 that are shown in FIG. 13.

Figure 15:
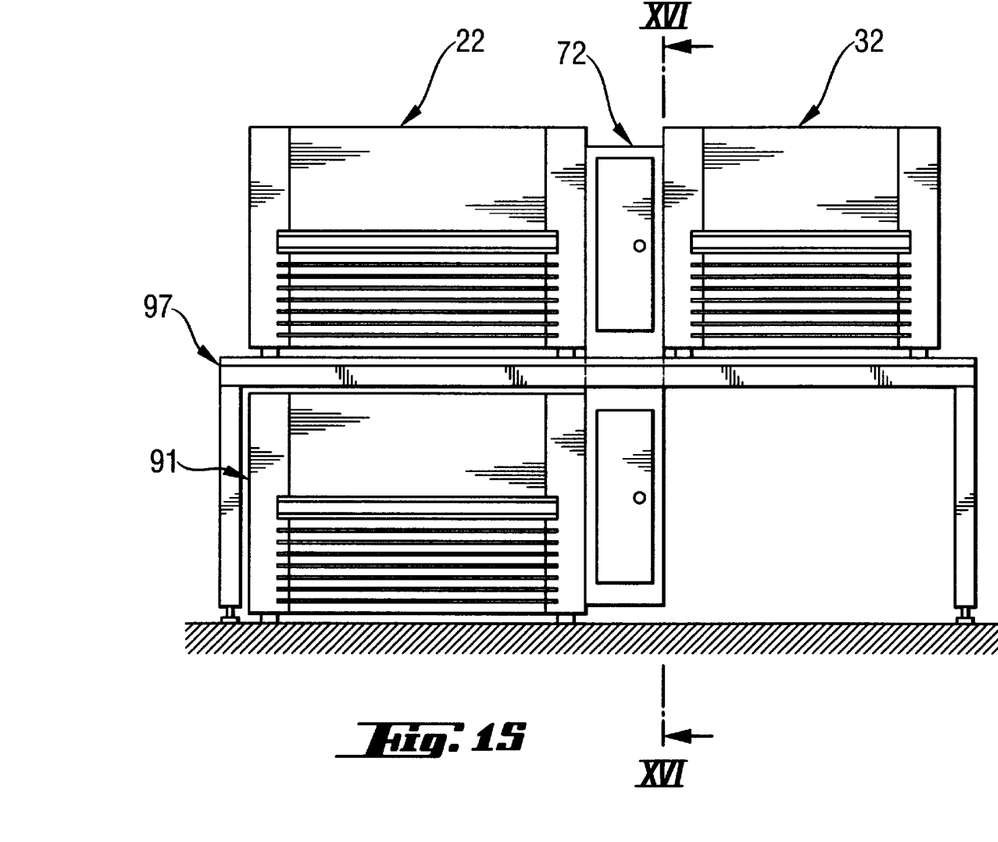
FIG. 15 is a schematic front view showing another embodiment of an apparatus according to the invention arranged between two apparatuses on one side and another apparatus on the opposite side, these three latter apparatuses forming part of an analyzer system.
Figure 16:
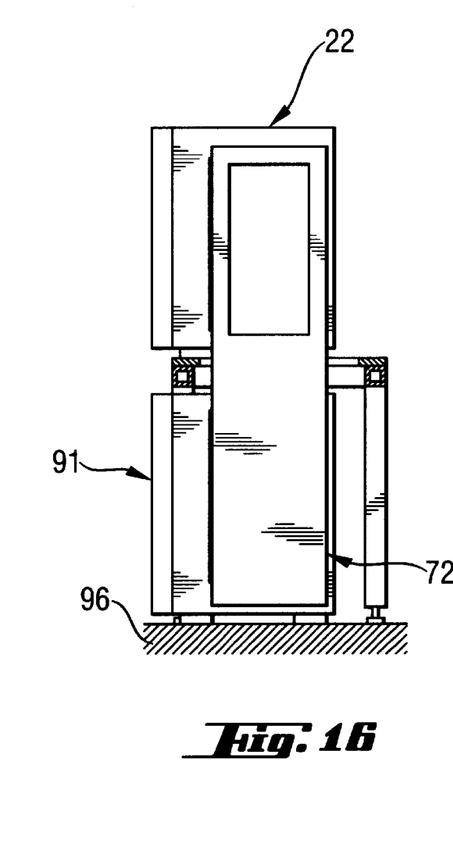
FIG. 16 is a schematic cross-sectional view in plane XVI—XVI of apparatuses shown in FIG. 15.

FIG. 15 shows a second configuration wherein a second embodiment of an apparatus 72 according to the invention is arranged between apparatuses 22 and 91 on one side and an apparatus 32 on the opposite side. Apparatuses 22, 91 and 32 form part of an analyzer system. Apparatuses 22 and 32 are positioned on a table 97. Apparatus 91 is positioned under table 97. Apparatus 72 provides the means for transporting a component carrier of the type described above between all three apparatuses 22, 91 and 32. FIG. 16 is a side view of apparatuses 72, 22 and 91 that are shown in FIG. 15.

Apparatus 72 shown in FIGS. 15 and 16 is longer than apparatus 11 shown in FIGS. 13 and 14. As shown in these figures, apparatus 11 is preferably used for transporting a component carrier 12 between two apparatuses 22 and 32 which form part of an analyzer system, whereas apparatus 72 is preferably used for transporting a component carrier 12 between three apparatuses 22, 32 and 91 which form part of an analyzer system.

Figure 17:
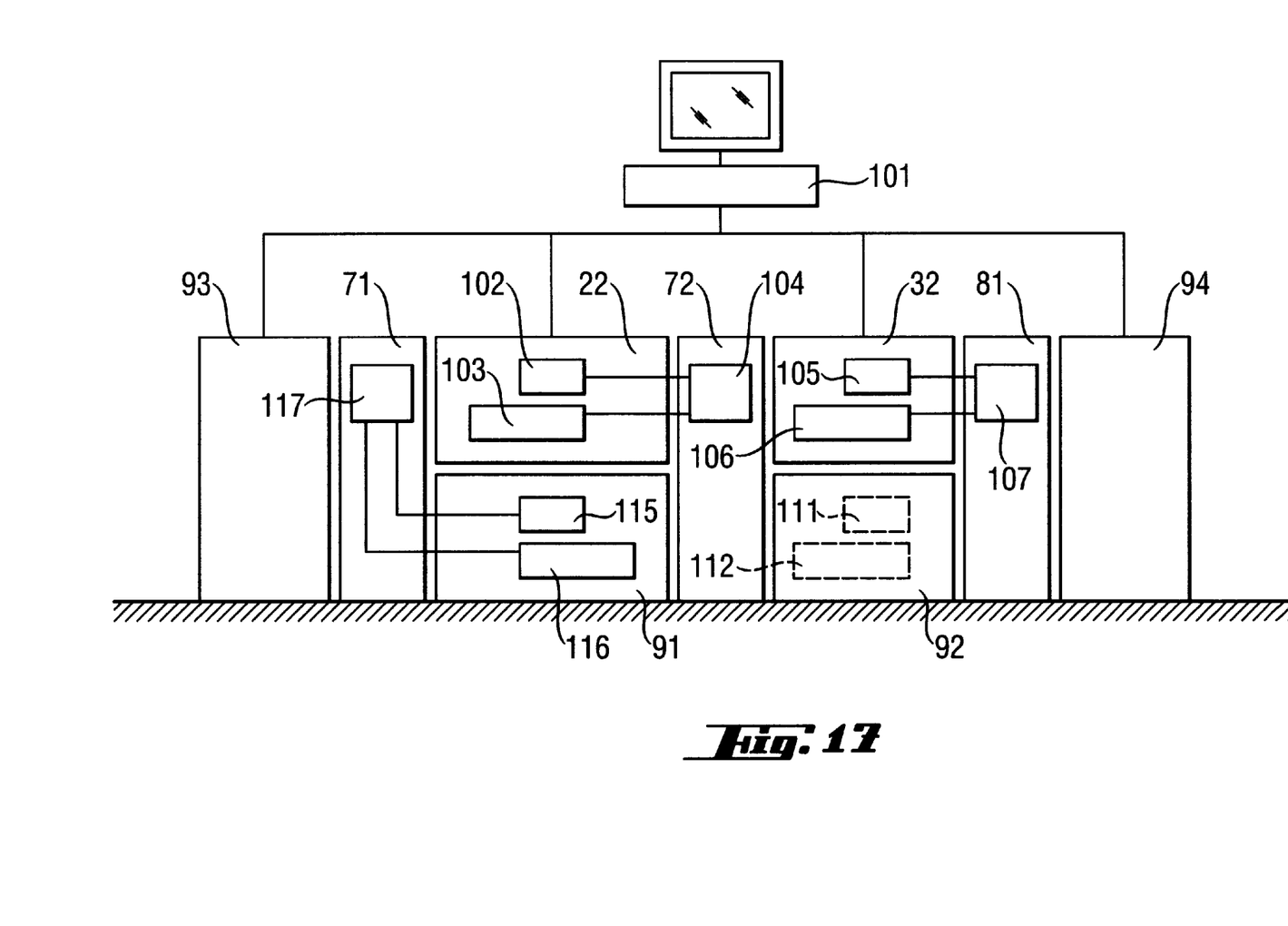
FIG. 17 is a block diagram of an analyzer system comprising several apparatuses according to the invention.

FIG. 17 shows a block diagram of an analyzer system comprising several apparatuses 71, 72, and 81 according to the invention and a number of apparatuses 22, 32, 91, 92, 93, and 94 which form part of the analyzer system and which are connected to a central processing unit (CPU) 101. The operation of each of the apparatuses 71, 72, and 81 is controlled by the control unit (CPU) of one of the apparatuses of the analyzer system to which it is connected. For instance, the operation of apparatus 72, which provides transport of a component carrier 12 between apparatuses 22, 32 and 91, is controlled by block 104, which in turn is controlled by CPU 102 of apparatus 22. Block 104 receives energy from power supply 103 of apparatus 22. In a similar way, the operation of apparatus 81, which provides transport of a component carrier between apparatuses 32, 92 and 94, is controlled by block 107, which in turn is controlled by CPU 105 of apparatus 32. Block 107 receives energy from power supply 106 of apparatus 32. Similarly, the operation of apparatus 71, which provides transport of a component carrier between apparatuses 22, 91 and 93, is controlled by block 117, which in turn is controlled by the CPU 115 of apparatus 91. Block 117 receives energy from power supply 116 of apparatus 91.

Apparatus 92 comprises a CPU 111 and a power supply 112 which are not connected to the CPU of any of the apparatuses 71, 72, and 81.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus may be varied substantially without departing from the spirit of the invention and the exclusive use of all modifications which come within the scope of the appended claims is reserved.

What is claimed is:

1. An apparatus for transporting components within an automatic analyzer system, said apparatus comprising:

a transport mechanism for moving a component carrier between a first apparatus for providing a first function in said system and a second apparatus for providing a second function in said system, said transport mechanism including a movable tray adapted to receive and transport said component carrier placed thereon, said component carrier being removable from said tray and being suitable for holding at least one of said components to be analyzed by said system, and said movable tray and said component carrier utilizing magnetic forces to maintain said component carrier in its position on said tray during movement of said tray between said first and second apparatus.

2. An apparatus according to claim 1 wherein a selected one of the tray and the component carrier includes a magnet.

3. An apparatus according to claim 1 wherein said component carrier is a hollow box with various openings and chambers suitable for holding a plurality of components of different shapes and sizes, said box having a bottom wall the outer surface of which comprises at least one metallic part which is capable of being held by a magnetic force.

4. An apparatus according to claim 3 wherein said transport mechanism moves said component carrier between a first position in said first apparatus and a second position in said second apparatus and each such apparatus comprises a loading bay for receiving said component carrier when brought thereto by said transport means, the loading bay of said first apparatus defining said first position and the loading bay of said second apparatus defining said second position.

5. An apparatus according to claim 3 wherein said movable tray has an upper surface which is at least partially covered by magnetic foil.

6. An apparatus according to claim 1 wherein said transport mechanism moves said component carrier between a first position in said first apparatus and a second position in said second apparatus and each such apparatus comprises a loading bay for receiving said component carrier when brought thereto by said transport means, the loading bay of said first apparatus defining said first position and the loading bay of said second apparatus defining said second position.

7. An apparatus according to claim 6 wherein said movable tray has an upper surface which is at least partially covered by magnetic foil.

8. An apparatus according to claim 6 wherein said transport mechanism further comprise a first transport device for moving said tray in a horizontal direction towards and away from each of said loading bays.

9. An apparatus according to claim 8 wherein said first transport device is a telescopic arm and said tray is attached to a movable part of said telescopic arm.

10. An apparatus according to claim 8 wherein said transport mechanism comprises a second transport device for moving said first transport device upwards and downwards in a vertical direction.

11. An apparatus according to claim 6 wherein said component carrier and said loading bay comprise means which attract each other by magnetic force and contribute to accurately define the predetermined position of said carrier with respect to said loading bay.

12. An apparatus according to claim 6 wherein each of the loading bays comprises guide surfaces which guide said component carrier towards said first position in said first loading bay and said second position in said second loading bay.

13. An apparatus according to claim 1 wherein said movable tray has an upper surface which is at least partially covered by magnetic foil.

14. An apparatus according to claim 1 wherein said transport mechanism is controlled by a control unit included in said first apparatus which forms part of the analyzer system.

15. An apparatus according to claim 1 wherein said transport mechanism provides movement in at least two orthogonal directions and said movable tray and said component carrier utilizing magnetic forces to maintain said component carrier in its position on said tray in each of said directions.

16. An apparatus according to claim 1 wherein said first apparatus provides said first function at a first location and said second apparatus provides said second function at a second location and said carrier utilizes magnetic forces to maintain itself in at least one of the first and second positions.

17. An apparatus according to claim 16 wherein said first apparatus has a first housing, said second apparatus has a second housing and said transport mechanism has a transport housing, said transport housing, said first housing and said second housing each incorporating connection means for connecting and aligning said first housing and said second housing to said transport housing.

18. An apparatus according to claim 1 wherein said first apparatus has a first housing, said second apparatus has a second housing and said transport mechanism has a transport housing, said transport housing, said first housing and said second housing each incorporating connection means for connecting and aligning said first housing and said second housing to said transport housing.

19. An apparatus for transporting components within an automatic analyzer system, said apparatus comprising:
a transport mechanism for moving a component carrier disposed thereon between a first apparatus and a second apparatus, said component carrier being suitable for holding at least one of said component to be analyzed by said system, said first apparatus providing a first function to said components when disposed in a first position and said second apparatus providing a second function to said components when disposed in a second position therein, and
said carrier utilizing magnetic forces to maintain itself in at least one of the first and second positions.

20. An apparatus of claim 19 wherein said transport mechanism also uses magnetic forces to maintain said component carrier in a predetermined position on said mechanism as it is transported from said first position to said second position.

21. An apparatus of claim 19 wherein said predetermined one of said first and second positions includes a surface and a selected one of this surface and said component carrier includes a magnet.

22. An apparatus of claim 19 wherein said first apparatus has a first housing, said second apparatus has a second housing and said transport mechanism has a transport housing, said transport housing, said first housing, and said second housing each incorporating connection means for connecting and aligning said first housing and said second housing to said transport housing.

23. An apparatus for transporting components within an automatic analyzer system, said apparatus comprising:
a transport mechanism for moving a component carrier holding components to be analyzed between a first apparatus for providing a first function to said components and a second apparatus for providing a second function to said components, said first and second apparatus respectively having first and second housings,
a transport housing for said transport mechanism, said transport housing, the alignment of said first and second housings being such that said transport mechanism can transport components from a first predetermined location in said first apparatus to a second predetermined location in said second apparatus, said first housing, and said second housing each incorporating connection means for connecting and aligning said first housing and said second housing to said transport housing.

24. An automatic analyzer system, said system comprising:
(a) a first apparatus for providing a first function,
(b) a second apparatus for providing a second function,
(c) a transport mechanism for moving a component carrier between said first and said second apparatus, said transport mechanism including a movable tray adapted to receive and transport said component carrier placed thereon, said component carrier being removable from said tray and being suitable for holding at least one of said components to be analyzed by said system, said movable tray and carrier utilizing magnetic forces to maintain said component carrier in its position on said tray during movement of said tray between said first and second apparatus.

25. An automatic analyzer system, said system comprising:
(a) a first apparatus for providing a first function to said components when disposed in a first region therein,
(b) a second apparatus for providing a second function to said components when disposed in a second region therein,
(c) a transport mechanism for moving a component carrier between said first apparatus and said second apparatus, said transport mechanism including a movable tray adapted to receive and transport said component carrier placed thereon, said component carrier being suitable for holding at least one of said component to be analyzed by said system, said movable tray and carrier utilizing magnetic forces to maintain said component carrier in at least one of the first and second regions.

26. An automatic analyzer system, said system comprising:
(a) a first apparatus for providing a first function and having a first housing,
(b) a second apparatus for providing a second function and having a second housing,
(c) transport mechanism disposed inside a transport housing, the alignment of said first and second housing being such that said transport mechanism can transport components from a first predetermined location in said first apparatus to a second predetermined location in said second apparatus, said transport housing, said first housing, and said second housing each incorporating connection means for connecting and aligning said first housing and said second housing to said transport housing.

* * * * *